United States Patent [19]

Kopietz et al.

[11] Patent Number: 5,536,831
[45] Date of Patent: Jul. 16, 1996

[54] OBTAINING CAPROLACTAM BY CLEAVAGE OF MOLTEN POLYCAPROLACTAM

[75] Inventors: Michael Kopietz, Grünstadt, Germany; Alan Handerman, Asheville, N.C.; Simon Jones, Leimen, Germany; Ulrich Kalck, Neuhofen, Germany; Claus-Ulrich Priester, Ludwigshafen, Germany; Heinz Auer, Neulussheim, Germany; Josef Ritz; Hugo Fuchs, both of Ludwigshafen, Germany; Paul Pijl, Frankenthal, Germany

[73] Assignee: BASF Aktiengesellschaft, Ludwigshafen, Germany

[21] Appl. No.: 355,285

[22] Filed: Dec. 12, 1994

[51] Int. Cl.$^6$ .................................................. C07D 201/12
[52] U.S. Cl. ................................... 540/540; 540/485
[58] Field of Search ............................... 540/540, 485

[56] References Cited

U.S. PATENT DOCUMENTS

| 5,233,037 | 8/1992 | Nielinger | 540/540 |
| 5,266,694 | 11/1993 | Moran | 540/540 |

FOREIGN PATENT DOCUMENTS

| 1978/05 | 11/1976 | Japan | 540/540 |
| 1979/01 | 11/1979 | Japan | 540/540 |

Primary Examiner—Robert T. Bond
Attorney, Agent, or Firm—Keil & Weinkauf

[57] ABSTRACT

Caprolactam is obtained from caprolactam-containing polymers in the presence of a base under reduced pressure by depolymerizing polymers which contain the repeating unit —[—N(H)—(CH$_2$)$_5$—C(O)—] or mixtures consisting essentially of from 50 to 99.99% by weight of a polymer containing the repeating unit —[—N(H)—(CH$_2$)$_5$—C(O)—]— from 0.01 to 50% by weight of additives selected from the group consisting of inorganic fillers, organic and inorganic pigments and dyes, from 0 to 10% by weight of organic and/or inorganic additives, from 0 to 40% by weight of non-polyamide-containing polymers and from 0 to 20% by weight of polyamides, with the exception of polycaprolactam and copolyamides prepared from caprolactam, in at least two depolymerization reactors connected in series.

6 Claims, 1 Drawing Sheet

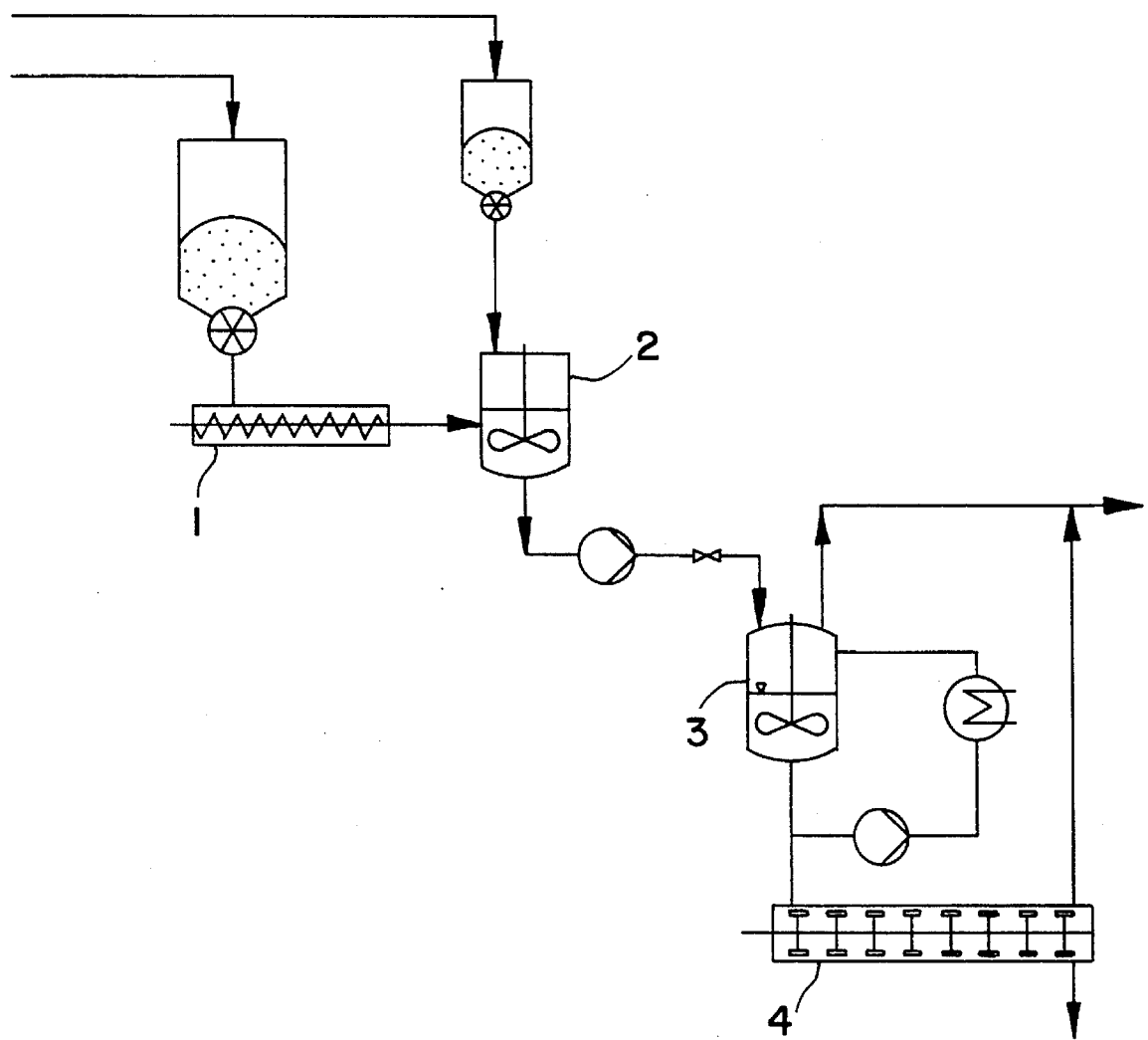

OBTAINING CAPROLACTAM BY CLEAVAGE OF MOLTEN POLYCAPROLACTAM

The present invention relates to a process for obtaining caprolactam from caprolactam-containing polymers in the presence of a base under reduced pressure.

The present invention furthermore relates to an apparatus for carrying out this process, the use of the process for recycling caprolactam-containing wastes and the use of the apparatus for obtaining caprolactam from polycaprolactam.

J. Appl. P. Sci. 22 (1978), 361–368 describes the cleavage of polycaprolactam (PA 6) in the presence of bases at reduced pressure. However, the yield of 90.5% is insufficient for large-scale industrial and economical use.

Furthermore, for example, JP 50131979 and JP 551002 disclose processes for the cleavage of PA 6 to give polycaprolactam, in which the reaction is carried out at reduced pressure in the presence of acids. However, in these cases also, the yields of 89 and 69%, respectively, are too unsatisfactory for economical use. Furthermore, all publications describe only the depolymerization of pure caprolactam.

Moreover, U.S. Pat. No. 5,169,870 describes the processing of prepared carpets with the aid of phosphoric acid cleavage. The disadvantage of this process is the high consumption of phosphoric acid, since the latter reacts with the calcium carbonate present in the carpeting.

It is an object of the present invention to provide a process for obtaining caprolactam from polycaprolactam which gives higher yields of caprolactam. Furthermore, it was intended to provide a process which permits the utilization of polycaprolactam-containing wastes to obtain caprolactam. Moreover, the catalysts used should be inert to the most commonly employed additives.

We have found that this object is achieved by a process for obtaining caprolactam from caprolactam-containing polymers in the presence of a base under reduced pressure by depolymerizing polymers which contain the repeating unit

or mixtures consisting essentially of from 50 to 99.99% by weight of a polymer containing the repeating unit —[—N(H)—(CH₂)₅—C(O)—]—

0.01 to 50% by weight of additives selected from the group consisting of inorganic fillers, organic and inorganic pigments and dyes, from 0 to 10% by weight of organic and/or inorganic additives, from 0 to 40% by weight of non-polyamide-containing polymers and from 0 to 20% by weight of polyamides, with the exception of polycaprolactam and copolyamides prepared from caprolactam, in at least two depolymerization reactors connected in series.

We have also found an apparatus for carrying out the novel process and the use of this apparatus and of the novel process for recycling polycaprolactam-containing wastes.

According to the invention, the starting materials used are polymers which contain the repeating unit

or mixtures consisting essentially of from 50 to 99.9, preferably from 60 to 99.99%, by weight of a polymer containing the repeating unit

from 0 to 50, preferably from 0 to 40%, by weight of additives selected from the group consisting of inorganic fillers, organic and inorganic pigments and dyes, from 0 to 10, preferably from 0 to 5%, by weight of organic and/or inorganic additives, from 0.01 to 40, preferably from 0.01 to 20%, by weight of non-polyamide-containing polymers and from 0 to 20, preferably from 0 to 15%, by weight of polyamides, with the exception of polycaprolactam and copolyamides prepared from caprolactam.

The preferably used polymer is polycaprolactam having a relative viscosity of from 1 to 5, preferably from 2.0 to 4.0 (measured at a concentration of 1 g of polymer per 100 ml in 96% strength by weight sulfuric acid at 25° C.). It is also possible to use oligomer residues or oligomer-containing polycaprolactam, each of which contains oligomers in an amount of from 0.01 to 100, preferably from 0.05 to 10, particularly preferably from 1 to 5%, by weight, based on the total amount.

Furthermore, copolyamides obtained from caprolactam and other polyamide-forming monomers, for example salts formed from a dicarboxylic acid, such as adipic acid, sebacic acid and terephthalic acid, and a diamine, such as hexamethylenediamine and tetramethylenediamine, preferably AH salt (obtained from adipic acid and hexamethylenediamine), and lactams, such as laurolactam, may also be used.

Observations to date have shown that all known polycaprolactams can be converted into caprolactam by the novel process, for example even a polycaprolactam which was prepared in the presence of mono- or dicarboxylic acids, or amines, such as triacetonediamine and hexamethylenediamine, which act as chain regulators, for example acetic acid, propionic acid, benzoic acid, $C_4$–$C_{10}$-alkanedicarboxylic acids, such as adipic acid, pimelic acid, suberic acid, azelaic acid, sebacic acid, undecanedioic acid, dodecanedioic acid and mixtures thereof, $C_5$–$C_8$-cycloalkanedicarboxylic acids, such as cyclopentane- 1,3-dicarboxylic acid, cyclohexane-1,4-dicarboxylic acid and mixtures thereof, benzene- and naphthalenedicarboxylic acids which may carry up to two sulfo groups, including the corresponding alkali metal salts, and whose carboxyl groups are not adjacent, such as terephthalic acid, isophthalic acid, naphthalene-2,6-dicarboxylic acid, 5-sulfoisophthalic acid and their sodium and lithium salts and mixtures thereof, and 1,4-piperazinedi($C_1$–$C_6$-alkanedicarboxylic acids) such as 1,4-piperazinediacetic acid, 1,4-piperazinedipropionic acid, 1,4-piperazinedibutanoic acid, 1,4-piperazinedipentanoic acid and 1,4-piperazinedihexanoic acid.

Corresponding copolyamides are known to a person skilled in the art and can be prepared by processes which are described, for example, in WO 93/25736, DE-A 14 95 198 and DE-A 25 58 480.

Observations to date have shown that all fillers usually used in the compounding of polyamides, for example glass fibers, calcium carbonate and talc, may be employed as inorganic fillers. Observations to date have shown that all pigments and dyes usually used for coloring polyamides, for example titanium dioxide, iron oxides or carbon blacks, and the conventional spinning dyes, such as chromium or copper complexes, may be employed as inorganic and organic pigments and dyes.

The conventional stabilizers and antioxidants, heat stabilizers and UV stabilizers, antistatic agents and flameproofing agents may be used as organic and inorganic additives.

Antioxidants and heat stabilizers are, for example, sterically hindered phenols, hydroquinones, phosphites and derivatives and substituted members of this group and mixtures of these compounds, as well as copper compounds, such as copper(II) iodide and copper(II) acetate.

Examples of UV stabilizers are substituted resorcinols, salicylates, benzotriazoles, benzophenones and compounds of the HALS (hindered amine light stabilizer) type, and manganese(II) compounds are also suitable for this purpose.

Conventional substances, for example polyalkylene oxides and derivatives thereof, may be used as antistatic agents.

Conventional chlorine- and nitrogen-containing compounds, such as melamine cyanurate and Dechlorane®, as well as aluminum hydroxide may be used as flameproofing agents.

Conventional thermoplastic engineering polymers, such as polymers based on ethylene, propylene, styrene and copolymers thereof with butadiene, may be used as non-polyamide-containing polymers.

Suitable polyamides with the exception of polycaprolactam and copolyamides prepared from caprolactam are, for example, polyamide 66, polyamide 610 and polyamide 46.

Preferred starting materials are polycaprolactam which is to be disposed of or wastes which are obtained in polycaprolactam production and the processing thereof to give filaments, films and injected molded or extruded parts, and shaped utility articles, such as films, packaging, fabric, carpeting fibers, filaments and extruded parts which are to be disposed of.

According to the invention, the base used is a compound selected from the group consisting of alkali metal oxide, alkali metal hydroxide, alkali metal carbonate, alkali metal alcoholate, alkaline earth metal oxide, alkaline earth metal hydroxide and alkaline earth metal carbonate, such as sodium oxide, potassium oxide, magnesium oxide, calcium oxide, sodium hydroxide, potassium hydroxide, calcium hydroxide, sodium carbonate, potassium carbonate, sodium methylate, calcium carbonate and magnesium carbonate, preferably sodium hydroxide, potassium hydroxide and a mixture of sodium hydroxide and potassium hydroxide.

The amount of base depends essentially on the basicity of the base to be used and, for example when sodium hydroxide and potassium hydroxide are used, is from 0.001 to 0.5, preferably from 0.005 to 0.05, kg per kg of polycaprolactam or caprolactam-donating polymer used.

The base may be added before, during or, preferably, after the melting procedure.

According to the invention, depolymerization is carried out in at least two, preferably two, depolymerization reactors connected in series. The depolymerization may also be carried out in one depolymerization reactor, preferably a paddle-type reactor, but the yield of caprolactam is higher in at least two depolymerization reactors.

Conventional stirred kettles may be used as the depolymerization reactor. The cleavage is usually carried out in the first stage at from 240° to 350° C., preferably from 250° to 310° C., and at from 0.05 to 8, preferably from 0.1 to 5, kPa, a continuous procedure advantageously being used.

The residence time in each of the depolymerization reactors is as a rule from 10 to 300, preferably from 20 to 200, minutes in the case of the continuous procedure.

In general, from 40 to 98, preferably from 65 to 85%, by weight of the polycaprolactam used are cleaved in the first depolymerization reactor D1.

In a preferred embodiment, a paddle-type reactor is used as the second depolymerization reactor, and the reaction conditions maintained are as a rule the same as those in the first depolymerization reactor, it being possible, if desired, to choose a higher temperature range, preferably from 260° to 320° C. If desired, further base may be introduced into the second reactor, for example by means of a metering apparatus. In principle, it is possible to use more than two depolymerization reactors, but of course the technical complexity increases as a result and it is therefore preferable to use only two depolymerization reactors connected in series.

In a further preferred embodiment, any oligomers of caprolactam which may be present after the depolymerization are separated from caprolactam obtained in the depolymerization and are fed to at least one of the depolymerization reactors.

In a further preferred embodiment, the following steps are carried out (cf. FIG. 1):

(a) melting of a polymer containing the repeating unit —(—NCH)—(CH$_2$)$_5$—C(O)—]— or a mixture consisting essentially of from 50 to 99.99% by weight of a polymer containing the repeating unit —[—N(H)—(CH$_2$)$_5$—C(O)—]— from 0.01 to 50% by weight of additives selected from the group consisting of inorganic fillers, organic and inorganic pigments and dyes, from 0 to 10% by weight of organic and/or inorganic additives, from 0 to 40% by weight of non-polyamide-containing polymers and from 0 to 20% by weight of polyamides, with the exception of polycaprolactam and copolyamides prepared from caprolactam, (b) introduction of the melt A into a depolymerization reactor D1 maintained under reduced pressure to give vapors B1 and a bottom product S1, (c) removal of the caprolactam-containing vapors B1 from the polymerization reactor D1 and (d) if required, transfer of the bottom product S1 to a second depolymerization reactor D2 maintained under reduced pressure to give caprolactam-containing vapors B2 and a bottom product S2, a base being added to the polymer, to the mixture or to the melt before, during or after the melting procedure but before the depolymerization, and stage (d) preferably being employed.

In a further, particularly preferred embodiment, the following steps may additionally be carried out:

(e) if required, passage of the vapors B1 and B2 each to an apparatus to remove any oligomers of caprolactam which may be present to give oligomers of caprolactam and caprolactam, or (f) combination of the vapors B1 and B2 and, if required, subsequent passage of the combined vapors through an apparatus to remove any oligomers of caprolactam which may be present to give oligomers of caprolactam and caprolactam, (g) recycling of the oligomers obtained under (e) or (f) into at least one of the depolymerization reactors D1 or D2, (h) if desired, combination of the caprolactam obtained under (e) or (f) and (i) if desired, transfer of the caprolactam obtained in stage h) to a purification stage.

The polymers or corresponding mixtures to be depolymerized (referred to below merely as polycaprolactam for short) can be melted in conventional melting apparatuses known to a person skilled in the art, at from 240° to 350° C., preferably from 250° to 310° C., to give the melt A. Extruders, in particular devolatilization extruders, are preferably used for this purpose, the preferably comminuted polycaprolactam being fed to said extruder.

In a preferred embodiment, the base is added to the molten polycaprolactam, the melt A advantageously being fed, after the melting procedure, to a mixing apparatus suitable for this purpose, for example a stirred kettle, and stirring being carried out during the addition of the base, to give a melt B.

In a further preferred embodiment, water present is removed from the base-containing melt B before the depolymerization, by subjecting the melt B to a reduced pressure of from 0.05 to 50 kPa and a temperature of from 240° to 320° C. For example, the water can be removed by devolatilization under reduced pressure in an extruder. This method can of course also be used to dewater even the melt A itself, by applying reduced pressure by means of a vacuum apparatus at one or more extruder orifices during the melting procedure.

During the dewatering, the water content is preferably brought to less than 0.1% by weight. The melt B, which, if desired, is dewatered, is fed, according to the invention, to the depolymerization reactor D1.

According to the invention, the melt A (containing the base) is subjected to reduced pressure in the depolymerization reactor D1. The resulting caprolactam is usually removed continuously from the first reactor with any other volatile components, such as oligomers of caprolactam (vapors B1).

The non-cleavable and uncleaved components (bottom product S1) are preferably transferred to a second depolymerization reactor D2 likewise maintained under reduced pressure, it being possible, if desired, also to introduce further base into the second depolymerization reactor.

As in the case of vapors B1, the vapors B2 obtained from the second reactor generally contain caprolactam and may contain further volatile components, such as oligomers of caprolactam. The bottom product S2 of the second depolymerization reactor D2 is preferably disposed of.

The caprolactam-containing vapors B1 and B2 obtained in the cleavage in the depolymerization reactors D1 and, if desired, D2 are fed in general to a purification stage.

The bottom product S1 obtained in the cleavage in the first depolymerization reactor D1 consists, as a rule, of a melt which is enriched essentially with inorganic residues and foreign polymers, ie. polymers which do not contain the repeating unit —[—N(H)—(CH$_2$)$_5$—C(O)—]—, and which in general also contains from 2 to 60, preferably from 15 to 35%, by weight of the caprolactam used upstream of the first depolymerization reactor D1.

In a further preferred embodiment, the temperature in the depolymerization reactor D1 is controlled by passing some of the reactor content via an external heat exchanger and then recycling it into the reactor (cf. FIG. 1).

The volatile components (vapors B2) obtained in the second, preferably present depolymerization reactor D2 are advantageously fed, preferably in combination with the vapors B1, to a purification stage for caprolactam. The bottom product S2 of the second depolymerization reactor D2, containing in general from 0.5 to 50% by weight of caprolactam and its degradation products present in equilibrium under the reaction conditions, is as a rule disposed of, for example in an incineration plant.

In a preferred embodiment, the non-caprolactam-containing components, in particular oligomers of caprolactam, are removed from the vapors B1 or B2, which if desired are combined, before these vapors are fed to a purification stage for caprolactam. The non-caprolactam-containing components separated off are preferably recycled to at least one of the depolymerization reactors.

Separation is usually carried out in a distillation apparatus, preferably in a dephlegmator, by cooling the vapors B1 and/or B2 to 50° to 200° C., preferably from 100° to 160° C., the pressure usually corresponding to that in the depolymerization reactors D1 and D2.

The purification of the caprolactam obtained according to the invention can be carried out by a conventional method, for example by feeding the caprolactam to a purification stage for caprolactam which is used in the preparation of caprolactam. Further possibilities for, if desired, purifying the caprolactam obtained according to the invention are disclosed, for example, in EPA 568,882 and 570,843. The purified caprolactam is then available generally for further use, in particular for the preparation of PA 6.

BRIEF DESCRIPTION OF THE DRAWING

The drawing is a schematic representation of apparatus for carrying out the inventive process.

The novel apparatus (cf. FIG. 1) consists essentially of a melting apparatus (1), a mixing apparatus (2) connected thereto and intended for mixing base and polycaprolactam melt, a depolymerization reactor D1 (3) downstream of the mixing apparatus (2) and a depolymerization reactor D2 (4) downstream of said reactor D1.

The novel apparatus is used for recycling caprolactam-containing wastes, preferably by the novel process.

The novel process is preferably used for recycling polycaprolactam-containing wastes.

The advantages of the novel process over prior art processes are cleavage yields of up to 99% and smaller amounts of wastes requiring treatment and disposal.

EXAMPLES

Example 1 (Batchwise Process)—Comparison

In a 1 l autoclave, 250 g of polyamide 6 (Ultramid® BS 700 (BASF), relative viscosity=2.7 (measured at a concentration of 1 g of polymer per 100 ml in 96% strength by weight sulfuric acid at 25° C.), having a residual moisture content of 0.01% by weight) and 5.0 g of sodium hydroxide were heated to 280° C. at 2 kPa. 232.6 g of caprolactam were removed from the autoclave by distillation in the course of 2 hours. Yield: 93%, oligomer content: 0.8% (determined by HPLC).

Examples 2 to 5 (Continuous)

1 kg/h of polycaprolactam or of a polycaprolactam-containing composition according to Table 1 was melted at 280° C. in an extruder (Barmag, L/D ratio 12:1). 20 g/h of potassium hydroxide were then mixed in a mixing apparatus (at 280° C., 50 kPa) with the melt discharged from the extruder, the entrained water simultaneously being removed under the stated conditions. The melt provided with the base was then fed to a depolymerization reactor D1 maintained under reduced pressure (1.5 kPa) and was subjected to cleavage at 273° C. and during an average residence time of 60 minutes. The bottom product S1 was transferred to a second depolymerization reactor (paddle-type reactor) (1.5 kPa, 273° C., residence time as in the first reactor) and the vapors B1 were combined with the vapors B2 from the second depolymerization reactor D2. The combined vapors B1 and B2 were analyzed by gas chromatography to determine their caprolactam content. The yields, based on caprolactam or copolymerized polycaprolactam etc used, are shown in Table 1.

TABLE 1

| Example | Substance used | Caprolactam [g/h] | Yield [%] | Oligomers [2] [%] |
|---|---|---|---|---|
| 2 | Ultramid ® BS 700 | 994 | 99 | — |
| 3 | Polycaprolactam concentrate[1] obtained from carpeting and containing 75% by weight of polycaprolactam | 701 | 93 | — |
| 4 | Copolyamide 6/66 (prepared from 85% by weight of caprolactam and 15% by weight of AH salt: Ultramid ® C 35, relative viscosity = 3.25) | 807 | 95 | — |
| 5 | Ultramid ® RC 6000 (containing 30.2% by weight of glass staple fibers; relative viscosity = 2.7) | 672 | 96 | — |

[1] The carpeting was freed from polyamide-free components until the polycaprolactam content was 75% by weight, based on the mixture.
[2] determined by HPLC

We claim:

1. A process for obtaining caprolactam from caprolactam-containing polymers in the presence of a base under reduced pressure, which comprises removing water from the caprolactam-containing polymers and thereafter depolymerizing the polymers which contain the repeating unit

—(—N(H)—(CH$_2$)$_5$—C(O)—)— or mixtures consisting essentially of from 50 to 99.9% by weight of a polymer containing the repeating unit —(—N(H)—(CH$_2$)$_5$—C(O)—)—

0.1 to 50% by weight of additives selected from the group consisting of inorganic fillers, organic and inorganic pigments and dyes, from 0 to 10% by weight of organic and/or inorganic additives, from 0 to 40% by weight of non-polyamide-containing polymers and from 0 to 20% by weight of polyamides, with the exception of polycaprolactam and copolyamides prepared from caprolactam, in at least two depolymerization reactors connected in series.

2. A process as defined in claim 1, wherein any oligomers of caprolactam which may be present after the depolymerization are separated from the caprolactam and fed to at least one of the depolymerization reactors for further depolymerization.

3. A process for obtaining caprolactam from caprolactam-containing polymers in the presence of a base under reduced pressure as defined in claim 1, wherein the following steps are included in the process:

(a) melting of a polymer containing the repeating unit —(—NCH)—(CH$_2$)$_5$—C(O)—)— or a mixture consisting essentially of from 50 to 99.9% by weight of a polymer containing the repeating unit —(—N(H)—(CH$_2$)$_5$—C(O)—)—

0.01 to 50% by weight of additives selected from the group consisting of inorganic fillers, organic and inorganic pigments and dyes from 0 to 10% by weight organic and inorganic additives, from 0 to 40% by weight of non-polyamide-containing polymers and from 0 to 20% by weight of polyamides, with the exception of polycaprolactam and copolyamides prepared from caprolactam, to give a melt A, (b) introduction of the melt A into a depolymerization reactor D1 maintained under reduced pressure to give vapors B1 and a bottom product S1, (c) removal of the caprolactam-containing vapors B1 from the polymerization reactor D1 and (d) if required, transfer of the bottom product S1 to a second depolymerization reactor D2 maintained under reduced pressure to give caprolactam-containing vapors B2 and a bottom product S2, a base being added to the polymer, to the mixture of to the melt before, during or after the melting procedure but before the depolymerization.

4. A process as defined in claim 1, wherein the base used is a compound selected from the group consisting of alkali metal oxide, alkali metal hydroxide, alkali metal carbonate, alkali metal alcoholate, alkaline earth metal oxide, alkaline earth metal hydroxide and alkaline earth metal carbonate.

5. An apparatus for obtaining caprolactam by cleaving molten polycaprolactam with a base under reduced pressure, consisting essentially of a melting apparatus (1), a mixing apparatus (2) connected thereto and intended for mixing base and polycaprolactam melt, a depolymerization reactor D1 (3) downstream of the mixing apparatus (2) and a depolymerization reactor D2 (4) downstream of said reactor D1.

6. A process as defined in claim 3, which includes the following additional steps:

(e) passage of the vapors B1 and B2 each to an apparatus to remove any oligomers of caprolactam which may be present to give oligomers of caprolactam and caprolactam, or (f) combination of the vapors B1 and B2 and, optionally, subsequent passage of the combined vapors through an apparatus to remove any oligomers of caprolactam which may be present to give oligomers of caprolactam and caprolactam, and (g) recycling of the oligomers obtained under (e) or (f) into at least one of the depolymerization reactors D1 or D2, (h) optionally, combination of the caprolactam obtained under (e) or (f) and (i) optionally, transfer of the caprolactam obtained in stage (h) to a purification stage.

* * * * *